United States Patent [19]
Lanier et al.

[11] Patent Number: 5,524,639
[45] Date of Patent: Jun. 11, 1996

[54] JAW SUPPORT APPARATUS

[76] Inventors: Paul F. Lanier, 2227 Arbor Crest, Carrollton, Tex. 75007; Lee H. Mota, 2970 Crystal Springs La., Richardson, Tex. 75082; Jacob C. Russler, III, 6824 Sherburne Dr., Dallas, Tex. 75231

[21] Appl. No.: 469,351

[22] Filed: Jun. 6, 1995

[51] Int. Cl.$^6$ .......................... A61G 15/00; A61F 5/37; A47C 20/00
[52] U.S. Cl. .................. 128/845; 128/870; 5/630
[58] Field of Search .................... 128/845, 846, 128/869, 870; 5/630, 636, 637, 640, 643; 27/13; 602/35, 36

[56] References Cited

U.S. PATENT DOCUMENTS

| | | | |
|---|---|---|---|
| 1,776,167 | 9/1930 | Stenshoel | 27/13 |
| 2,270,588 | 1/1942 | Hanson | 27/13 |
| 3,650,523 | 3/1972 | Darby | 128/870 |
| 5,154,186 | 10/1992 | Laurin | 128/870 |
| 5,263,494 | 11/1993 | Margelos | 128/845 |

*Primary Examiner*—Michael A. Brown
*Attorney, Agent, or Firm*—Fulbright & Jaworski

[57] ABSTRACT

An apparatus intended to maintain or improve a supine patient's airway in a hands-free environment. A frame and detachable pillow device are placed under the patient's head. Mechanisms extend laterally from the frame and provide jaw support members that may be brought under the angles of the jaw. The jaw support members may slide towards and away from the frame, but this sliding movement is regulated by a unidirectional clutch, such as a ratchet and pawl system, which restricts the jaw support members to sliding movement away from the frame only. When the jaw support members are slid away from the frame, they engage the angles of the jaw, and then thrust the jaw forward to maintain or improve the patient's airway. Once the desired anteriorly thrust position of the jaw is achieved, the unidirectional clutch holds the jaw in place until the clutch is released. The weight of the jaw then causes the jaw support members to slide back towards the frame, restoring the jaw to its normal position.

27 Claims, 4 Drawing Sheets

JAW SUPPORT APPARATUS

PREAMBLE

The present invention relates to an apparatus for supporting the jaw of a supine patient to maintain or improve the patient's airway, and was co-invented by the applicants: (1) Paul Lanier, of 2227 Arbor Springs, Carrollton, Tex. 75007; (2) Lee H. Mota, of 2970 Crystal Springs, Richardson, Tex. 75082; and (3) Chuck Russler, 11424 Chairman Drive, Dallas, Tex. 75243.

BACKGROUND OF THE INVENTION

A variety of situations arise in modern health care when it is required to maintain or improve a supine patient's airway without intubation. Such situations are common, for example, when transporting a partially or completely anesthetized supine patient to or from surgery. Other similar situations may arise in the emergency room, or in the recovery room after surgery. In such situations, intubation may not be desirable or even feasible due to the physical condition of the patient. Without intubation, however, several mechanisms can work to occlude the supine patient's airway, such as the pharynx collapsing, the tongue falling back into the throat, or the jaw simply falling back.

Up until now, health care professionals have countered these effects by using a procedure whereby the thumbs are placed on the patient's forehead and the fingers are placed behind the angles of the patient's jaw. When the health care professional rotates the wrist and pushes the fingers forward, the effect is to thrust the patient's jaw anteriorly. With the jaw in this artificial anterior position, the patient's airway is dramatically improved without intubation. The problem, however, is that this position with the hands now has to be maintained, disabling the health care professional from any other activity that requires use of the hands, and causing fatigue in hands and wrists of the health care professional.

The present invention is directed to an apparatus and a method that addresses this problem. A frame (with detachable pillow) is placed under the supine patient's head, secured to the patient's forehead if desired. Extensions attached to the frame emerge from under the back of the neck and run just above and parallel to the shoulders. Swinging members, pivoting about the far ends of the extensions, are then brought back towards the sides of the patient's neck, allowing jaw support members slidably attached to the ends of the swinging members to extend up under the angles of the patient's jaw.

Copying the effect of the health care professional's fingers when improving the airway as described above, the jaw support members are slid away from the frame, making contact with the angles of the patient's jaw and forcing the patient's jaw to be thrust forward anteriorly.

The slidable attachment of the jaw support members to the swinging members also includes a unidirectional clutch such as a ratchet and pawl system. Once the patient's jaw is thrust anteriorly to the position required to maintain or improve the airway, therefore, the unidirectional clutch keeps the jaw in this position until the clutch is released. At that time, if desired, the patient's head may then be tilted forward and the present invention removed.

Emergency removal of the present invention from the vicinity of the patient may also be accomplished by rotating the swinging members away from the patient until the jaw support members are clear. The patient's head may then be lifted momentarily and the entire apparatus removed quickly.

Related devices directed to supporting the human jaw from its angles are known in the field of undertaking. Morticians have patented devices intended to improve the appearance of supine corpses by modifying the position of the jaw with respect to the head. See, e.g., Stenshoel, U.S. Pat. No. 1,776,167; Hanson, U.S. Pat. No. 2,270,588. These devices do not solve the basic need addressed by the present invention, however, in that they are not directed to thrusting a patient's jaw anteriorly to maintain or improve the airway. Moreover, these devices are intended to hold the jaw semipermanently for long periods, whereas the present invention fulfills a need to release the jaw quickly if necessary in an emergency.

SUMMARY OF THE INVENTION

It is an object of the present invention to provide a means of maintaining or improving the airway of a supine patient by supporting the jaw from the angles and then thrusting it anteriorly.

It is a further object of this invention, once the jaw is thrust anteriorly, to support the jaw in that position in a hands-free environment.

It is a further object of this invention to support the jaw using a unidirectional clutch, so that the support for the jaw may be removed quickly and easily by releasing the clutch.

It is a further object of this invention to provide a means of clearing all mechanisms attached to the invention from the vicinity of the patient in the event of an emergency.

It is a further object of this invention to enhance control over the movement of the patient's head by providing an optional head restraint attached to the frame.

It is a further object of this invention to enhance the comfort of the patient by providing contact surfaces that are sculpted to fit the anatomy that they touch.

It is a further object of this invention to provide removable pillow and jaw cradles that may detached to be cleaned if necessary.

It is a further object of this invention to provide a pillow and jaw cradles that may be made from a variety of resilient materials.

It is a further object of this invention to provide a device that is relatively simple and inexpensive to manufacture, and yet sturdy and reliable in use.

These and other objects of the present invention will be apparent to those skilled in this art from the detailed description of a preferred embodiment of the invention set forth below.

BRIEF DESCRIPTION OF THE DRAWINGS

This invention will be further described in connection with the accompanying drawings, in which.

DETAILED DESCRIPTION OF THE INVENTION

Figure 1:
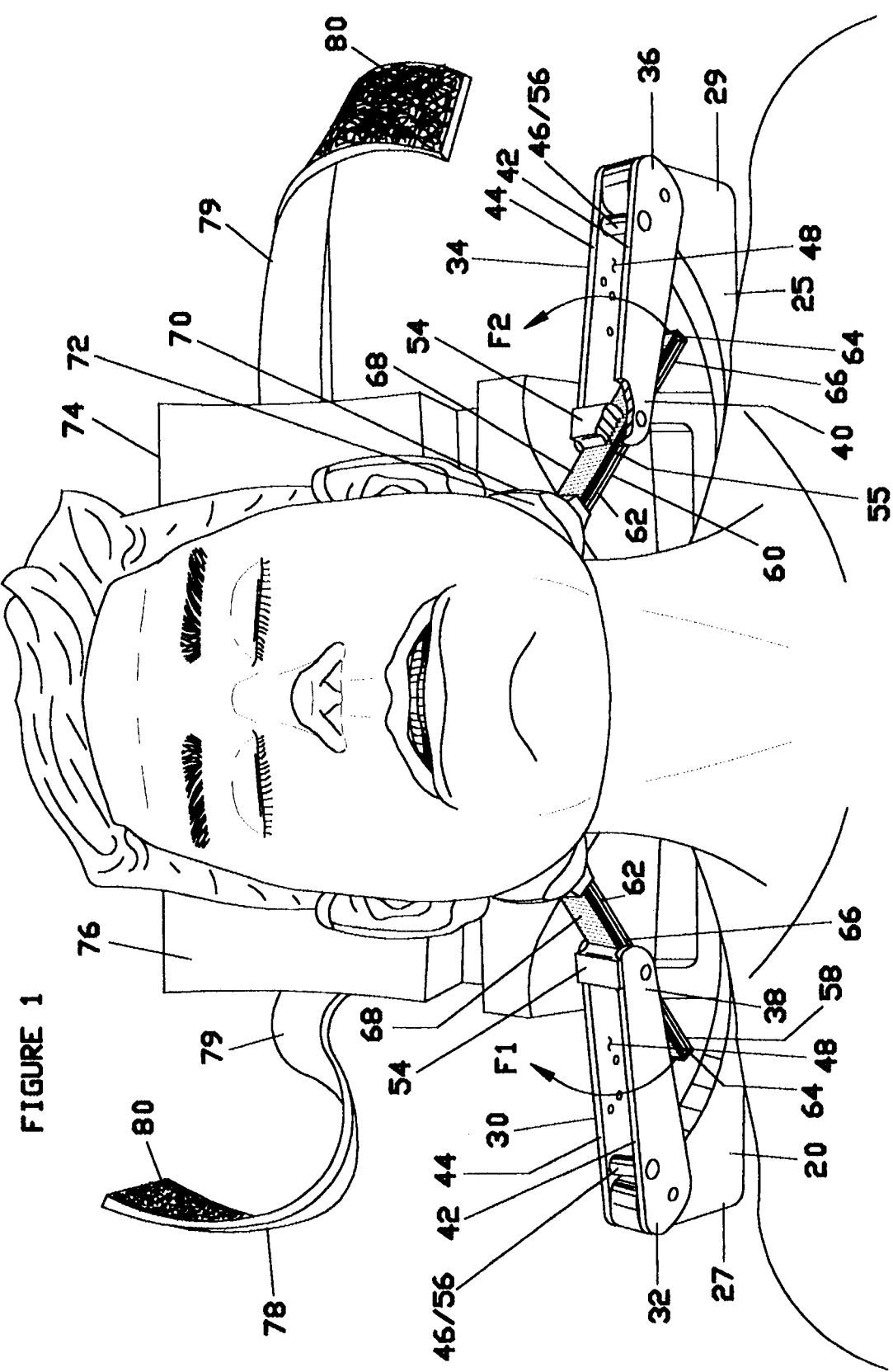
FIG. 1 is a top view looking down on a supine patient with the present invention in use. Front plate 42 and pawl means 54 of second swinging member 34 are partially cut away to reveal pawl face 55 engaging on straight ratchet means 68. Head restraint 78 is not in use.
Figure 2:
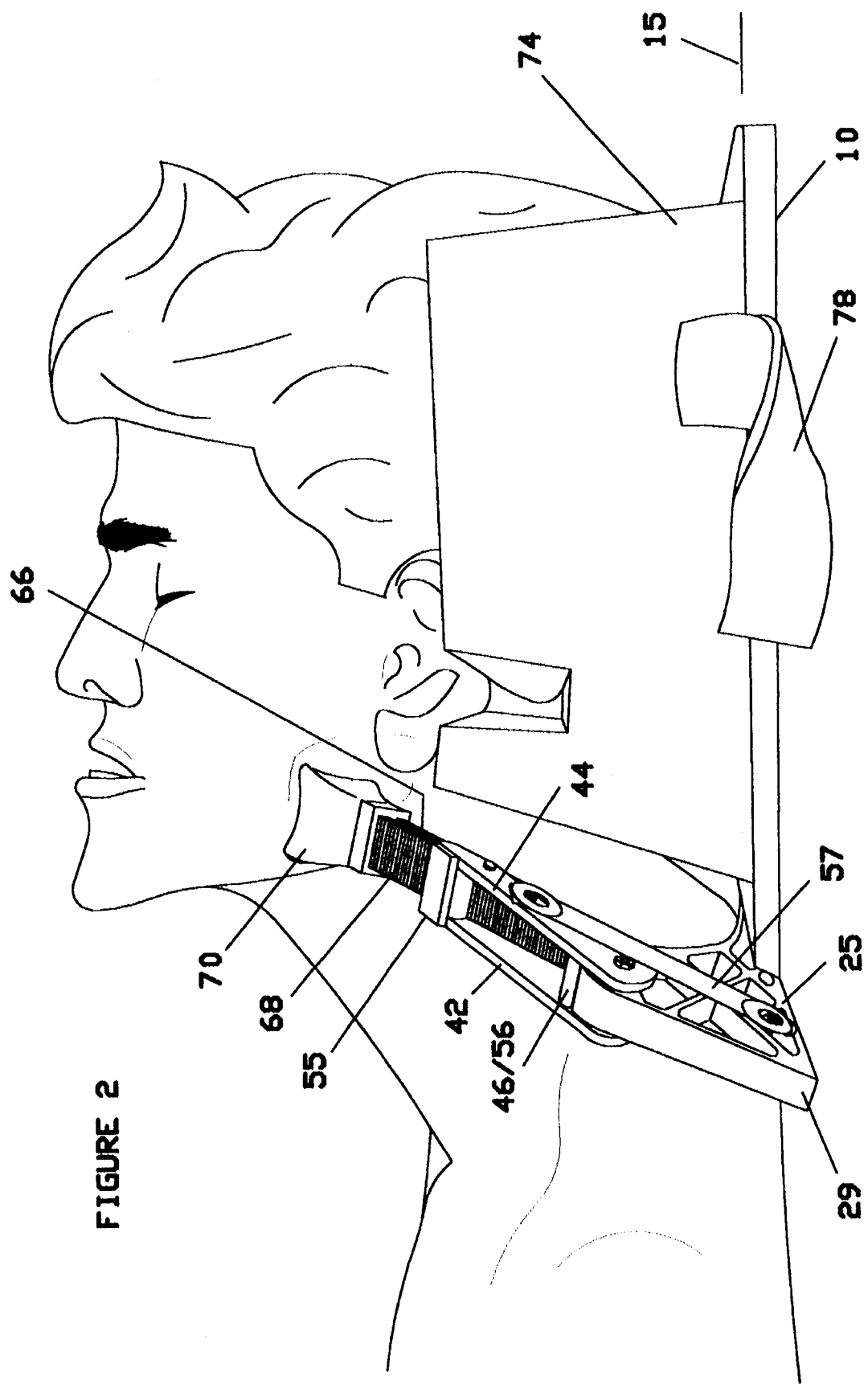
FIG. 2 is a side view of FIG. 1 looking from the patient's left side. Elastic means 57 are illustrated.
Figure 3:
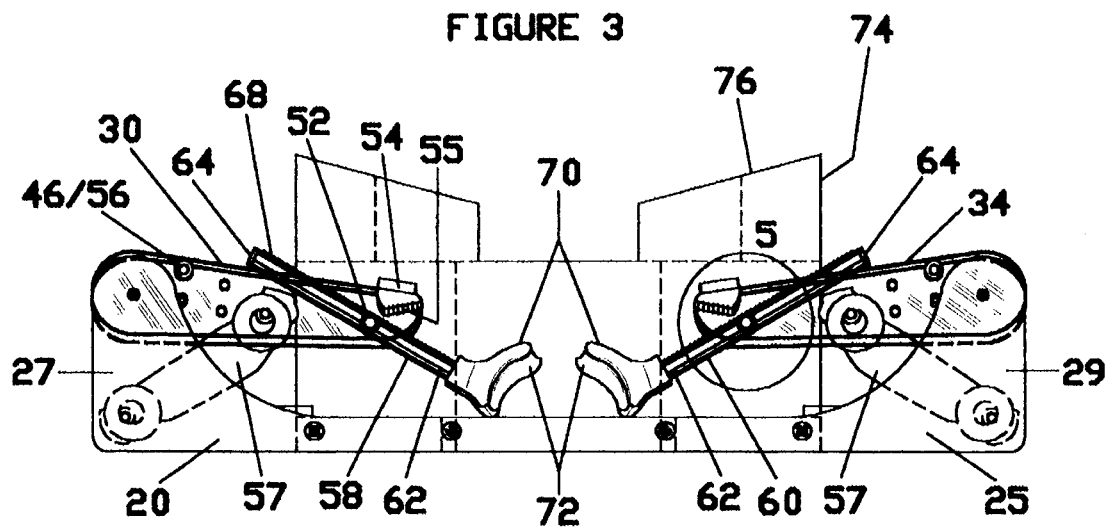
FIG. 3 is an elevation view of the present invention from the side normally under the patient's neck. The sculpted shapes of detachable pillow means 74 and jaw cradles 70 are illustrated. Swinging members 30 and 34 are illustrated "see-through" to display components otherwise hidden.
Figure 4:
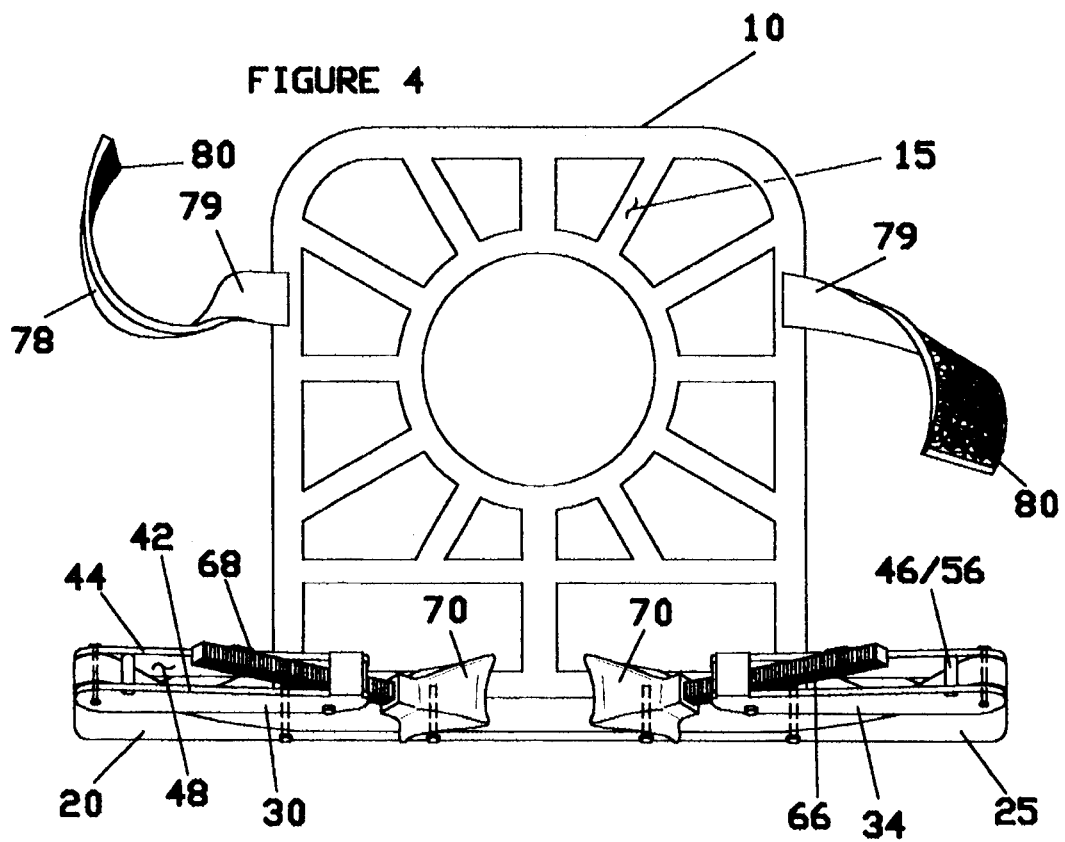
FIG. 4 is a top view of the present invention, without a patient, and with detachable pillow means 74 removed to reveal frame 10 in more detail.

With reference to FIGS. 2 and 4, frame 10 has an anterior face 15. FIGS. 1, 3 and 4 illustrate that frame 10 also has left extension member 20 and right extension member 25 connected thereto, left extension member 20 extending leftwardly from anterior face 15 of frame 10 and right extension member 25 extending rightwardly from anterior face 15 of frame 10. Extension members 20 and 25 also have far ends 27 and 29 respectively, far ends 27 and 29 located distant from frame 10. As shown in more detail on FIG. 1, first swinging member 30 is pivotally attached at its far end 32 to far end 27 of left extension member 20, and second swinging member 34 is pivotally attached at its far end 36 to far end 29 of right extension member 25 so that near ends 38 and 40 of first and second swinging members 30 and 34 may pivot to approach anterior face 15 of frame 10.

As further shown on FIGS. 1, 2 and 4, first swinging member 30 and second swinging member 34 each include a substantially dihedral front plate 42 and a substantially dihedral back plate 44. Front and back plates 42 and 44 are fixed rigidly together and separated by spacer means 46 to provide gaps 48. As shown in cutaway on FIG. 1, and in detail on FIGS. 5 and 5A, each gap 48 contains first boss 50 facing second boss 52, first boss 50 located on back plate 42 opposite second boss 52 located on front plate 44. Each gap 48 also provides pawl means 54 fixed within gap 48 and offering pawl face 55 available to be engaged upon from within gap 48. The preferred embodiment described herein, with dihedral plates 42 and 44 forming gaps 48, reflects the inventors' current understanding of the best mode of making the present invention. It will be understood that instead, however, first and second swinging members 30 and 34 could also be generally of a more solid construction, with facing bosses 50 and 52 located within slots or openings provided in swinging members 30 and 34, and that such an arrangement would not depart from the spirit and scope of the present invention.

FIGS. 1, 2, 3 and 4 also illustrate that each gap 48 also provides stop means 56, each stop means 56 defining a predetermined pivotal rest position for swinging members 30 and 34 with respect to left and right extension members 20 and 25 respectively as swinging members 30 and 34 approach anterior face 15 of frame 10. In the preferred embodiment herein, spacer means 46 are located within gaps 48 so that they may also serve as stop means 56. The present invention is not limited to this "dual purpose" configuration, however, and it is contemplated that spacer means 46 and stop means 56 may be separate components without departing from the spirit and scope of the present invention. With reference to FIGS. 2 and 3, elastic means 57 encourage swinging members 30 and 34 to approach anterior face 15 of frame 10 and make contact with stop means 56.

Figure 5:
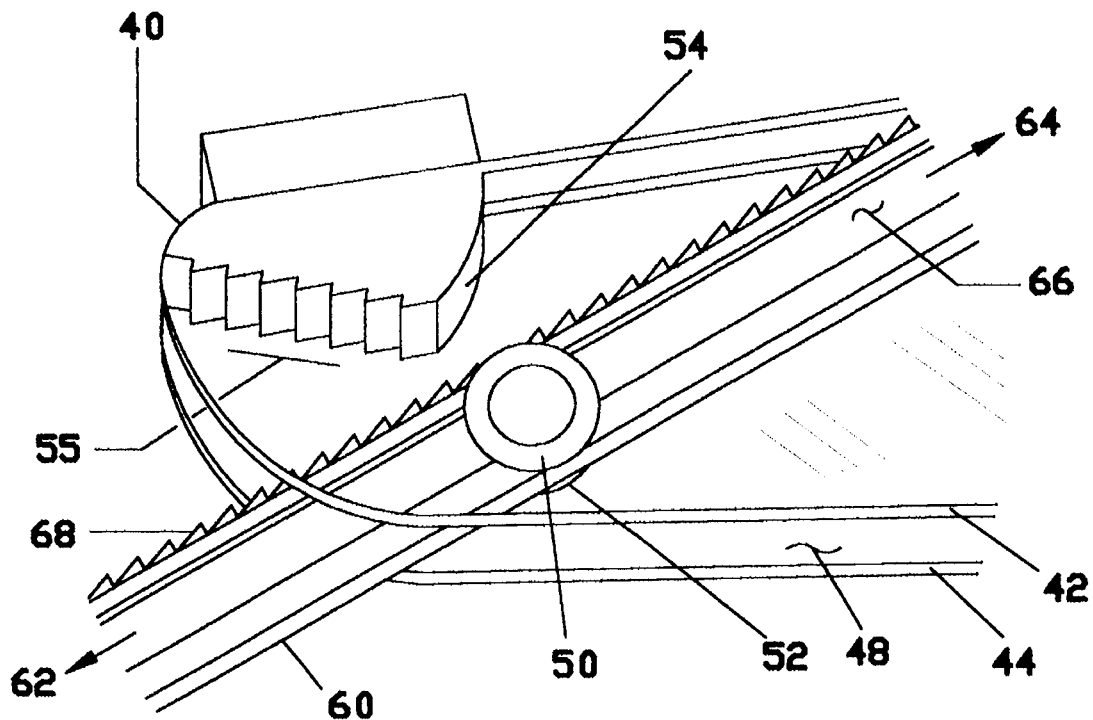
FIG. 5 is a detailed view of near end 40 of second swinging member 34, as taken from FIG. 3. Front plate 42 is shown "see-through" to display components in gap 48 more clearly.
Figure 5A:
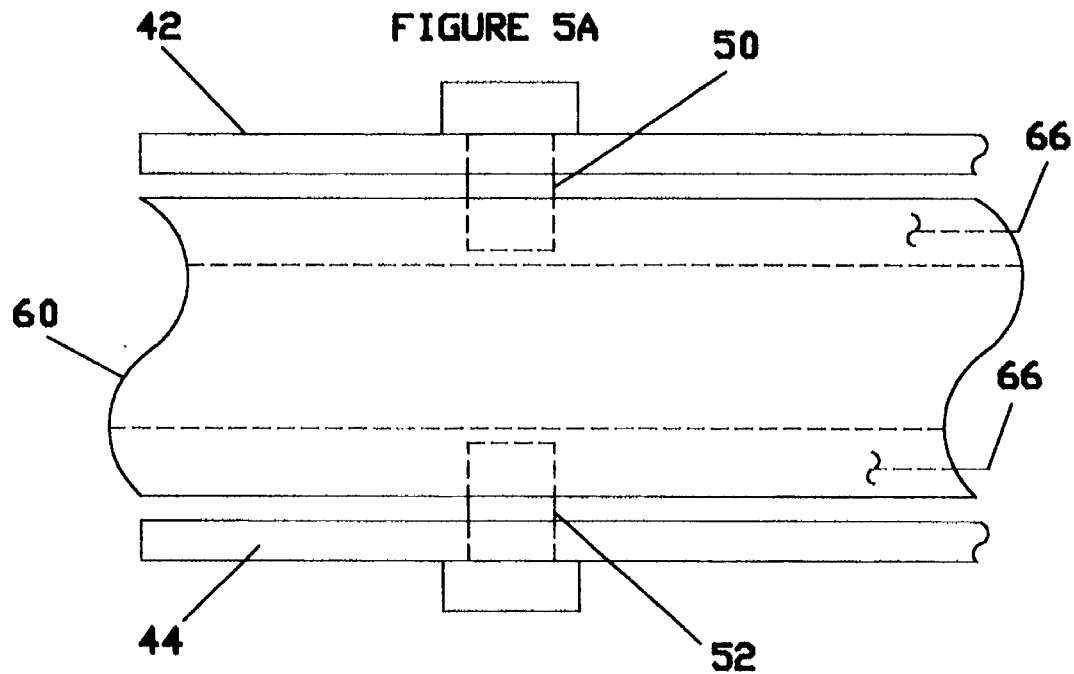
FIG. 5A is a view of FIG. 5 looking up from underneath.

Best seen on FIGS. 1, 5 and 5A, near end 38 of first swinging member 30 provides left jaw support member 58, while near end 40 of second swinging member 34 provides right jaw support member 60. Jaw support members 58 and 60 each have an anterior end 62 opposite a posterior end 64. Jaw support members 58 and 60 also each have two grooves 66 and a straight ratchet means 68 provided therein. Bosses 50 and 52 are each paired with a groove 66.

Referring now particularly to FIGS. 5 and 5A, left and right jaw support members 58 and 60 are then received into gaps 48 in first and second swinging members 30 and 34 respectively, each boss 50 and 52 also simultaneously received slidably into its paired groove 66 so as to permit jaw support members 58 and 60 to slide towards and away from anterior face 15 of frame 10. Left and right jaw support members 58 and 60 as received into gaps 48 also offer their straight ratchet means 68 to pawl faces 55, the straight ratchet means 68 and the pawl faces 55 oriented so as to restrict jaw support members 58 and 60 to sliding displacement away from anterior face 15 of frame 10 only.

FIG. 5 also illustrates that bosses 50 and 52 as received into grooves 66 will permit a predetermined amount of pivotal rotation of jaw support members 58 and 60 about bosses 50 and 52. This pivotal rotation is limited in one direction at the point when straight ratchet means 68 and pawl faces 55 fully engage, at which time jaw support members are restricted to sliding displacement away from anterior face 15 of frame 10 only. When pivotal rotation of jaw support members 58 and 60 is effectuated in the direction of arrows F1 and F2 as shown on FIG. 1, however, straight ratchet means 68 and pawl faces 55 eventually become fully disengaged, allowing free sliding displacement of jaw support members 58 and 60 towards anterior face 15 of frame 10.

Referring now to FIGS. 1, 2 and 3, jaw cradles 70 are attached to anterior ends 62 of jaw support members 58 and 60. Jaw contact surfaces 72 are sculpted to allow jaw cradles 70 to fit snugly when jaw cradles 70 are brought into contact with the angles of a patient's jaw. The preferred embodiment herein contemplates that jaw contact surfaces 72 will be made from a resilient material, including polyurethane, sponge or rubber, to enhance comfort of the patient while the present invention is in use. The preferred embodiment herein also contemplates that jaw cradles 70 may be removable to allow cleaning, although this feature could be optional. It will also be understood that the present invention could also function as intended, if necessary, with jaw cradles 70 removed, possibly in an emergency.

With further reference to FIGS. 1, 2 and 3, detachable pillow means 74 is attached to anterior face 15 of frame 10, whose head contact surface 76 is sculpted to fit the back of a supine head and neck snugly. Again, the preferred embodiment herein contemplates that head contact surface 76 will be made from a resilient material, including sponge, rubber or polyurethane, to enhance comfort of the patient while the present invention is in use. Again, as in reference to jaw cradles 70, it will be understood that the present invention could also function as intended, if necessary, with detachable pillow means 74 detached, possibly in an emergency.

Optional additional control over the movement of the patient's head while the present invention is in use may be achieved by using head restraint 78, which secures the forehead of the patient to pillow means 74 and frame 10. The preferred embodiment herein contemplates that if included, head restraint 78 could be of one of several types of construction, including two ties 79 fastened by contact friction grip means 80, as illustrated in FIGS. 1, 2 and. 4, or alternatively an elasticated band, or two ties knotted together, or buckled, or fastened by contact adhesive or by a hook-and-loop mechanism.

It will now be seen from FIGS. 1 and 2 that in order to operate the present invention, frame 10, as proffering detachable pillow means 74, may be placed under the head and neck of a supine patient so that left and right extension members 20 and 25 extend out from under the neck, above and substantially parallel with the shoulders. Head restraint 78 may be applied, if required or desired. Jaw support members 58 and 60, as proffering jaw cradles 70, may then be placed beneath the angles of the patient's jaw. The patient's jaw may then thrust anteriorly as the operator's hands cause jaw support members 58 and 60 to slide in a direction away from frame 10. Once the patient's jaw is in the desired position to improve the patient's airway, the operator's hands may be removed, and the weight of the patient's jaw will cause pawl faces 55 to engage upon straight ratchet means 68. Sliding displacement of jaw support members 58 and 60 back towards frame 10 will thereby be prevented, allowing the jaw to remain thrust forward and the airway to remain improved in a hands-free environment. Release of the jaw is effectuated by the operator rotating posterior ends 64 of jaw support members 58 and 60 about bosses 50 and 52 in directions F1 and F2 as shown on FIG. 1, thereby disengaging pawl faces 55 from straight ratchet means 68. With pawl faces 55 and straight ratchet means 68 so disengaged, the weight of the patient's jaw will cause jaw support members 58 and 60 to slide unimpeded towards frame 10 until the patient's jaw assumes a normal position. If necessary, emergency removal of the present invention away from the vicinity of the patient may then be accomplished by rotating first and second swinging members 30 and 34 so that near ends 38 and 40 thereof, along with jaw support members 58 and 60 attached thereto, are swung away from the patient and clear. The patient's head may then be elevated momentarily to remove the present invention out from underneath.

The invention has been shown, described and illustrated in substantial detail with reference to a presently preferred embodiment. However, it will be understood by those skilled in the art that changes and modifications may be made without departing from the spirit and scope of the invention which is defined by the claims set forth hereunder.

I claim:

1. A jaw support apparatus, comprising:

a frame, the frame having an anterior face;

a left extension member and a right extension member, the left extension member and the right extension member each having a near end and a far end, the near ends of the left extension member and the right extension member each connected to the frame, the left extension member extending leftwardly from the anterior face of the frame, the right extension member extending rightwardly from the anterior face of the frame;

first and second swinging members, both swinging members also having a near end and a far end, the far end of the first swinging member pivotally attached to the far end of the left extension member, the far end of the second swinging member pivotally attached to the far end of the right extension member, said pivotal attachments allowing the near ends of the first and second swinging members to approach the anterior face of the frame, the first swinging member and the second swinging member each including a substantially dihedral front plate and a substantially dihedral back plate fixed rigidly together and separated by spacer means, the front plates and the back plates each having a front side and a back side, the front side of the back plates facing the back side of the front plates, the spacer means providing gaps between the front plates and the back plates, each gap containing first and second bosses, the first boss located on the front side of the back plate and protruding partially into the gap, the second boss located on the back side of the front plate and also protruding partially into the gap, each gap also providing pawl means, the pawl means fixed within the gap and available to be engaged upon from within the gap;

first and second stop means, the first stop means defining a predetermined pivotal rest position for the first swinging member with respect to the left extension member as the first swinging member approaches the anterior face of the frame, the second stop means defining a predetermined pivotal rest position for the second swinging member with respect to the right extension member as the second swinging member approaches the anterior face of the frame;

first and second elastic means, the first elastic means provided between the first swinging member and the left extension member, the second elastic means provided between the second swinging member and the right extension member, each elastic means operating to encourage the swinging members to approach the anterior face of the frame;

a left jaw support member and a right jaw support member, both jaw support members having an anterior end opposite a posterior end, the left and right jaw support members also each providing two grooves, each boss in the gap in the first swinging member paired with a groove in the left jaw support member, each boss in the gap in the second swinging member paired with a groove in the right swinging member, the left and right jaw support members also each further providing straight ratchet means;

the left and right jaw support members received into the gaps in the first and second swinging members respectively, each boss in each gap also simultaneously received slidably into its paired groove so as to permit the jaw support members to slide towards and away from the anterior face of the frame, the left and right jaw support members as received into the gaps also offering their straight ratchet means to the pawl means in each gap, said straight ratchet means and said pawl means oriented so as to restrict the jaw support members to sliding displacement away from the anterior face of the frame only, the bosses as received into their grooves also permitting a predetermined amount of pivotal rotation of the jaw support members about the bosses, said pivotal rotation being permitted between a first travel limit and a second travel limit, the first travel limit being reached when the straight ratchet means and the pawl means fully engage, the second travel limit being reached when the straight ratchet means and the pawl means fully disengage;

first and second jaw cradles, the first jaw cradle removably attached to the anterior end of the left jaw support member, the second jaw cradle removably attached to the anterior end of the right jaw support member, the first and second jaw cradles also each having jaw contact surfaces, the jaw contact surfaces being sculpted to fit snugly when the jaw cradles are brought into contact with the angles of a jaw, the jaw contact surfaces being made from a polyurethane material;

detachable pillow means, the detachable pillow means removably attached to the anterior face of the frame, the detachable pillow means having a predetermined three-dimensional profile, said profile being sculpted to fit the back of a supine head and neck snugly, the detachable pillow means also being made from a sponge material; and means for restraining a head to the anterior face of the frame, said restraining means including two ties and a contact friction grip fastener means;

whereby the anterior face of the frame may be placed under a supine patient's head so that, when the anterior ends of the jaw support members are brought into contact with the angles of the patient's jaw and the patient's jaw is then pushed forward anteriorly, the straight ratchet means as engaged on the pawl means allow the jaw support members to slidably follow said anterior movement of the jaw and prevent retraction thereof, thereby maintaining or improving the patient's airway in a hands-free environment.

2. A jaw support apparatus, comprising:

a frame, the frame having an anterior face;

a left extension member and a right extension member, the left extension member and the right extension member each having a near end and a far end, the near ends of the left extension member and the right extension member each connected to the frame, the left extension member extending leftwardly from the anterior face of the frame, the right extension member extending rightwardly from the anterior face of the frame;

first and second swinging members, both swinging members also having a near end and a far end, the far end of the first swinging member pivotally attached to the far end of the left extension member, the far end of the second swinging member pivotally attached to the far end of the right extension member, said pivotal attachments allowing the near ends of the first and second swinging members to approach the anterior face of the frame;

a left jaw support member and a right jaw support member, both jaw support members having an anterior end opposite a posterior end, the left jaw support member slidably connected to the near end of the first swinging member, the right jaw support member slidably connected to the near end of the second swinging member, said slidable connections oriented to permit sliding displacement of the left and fight jaw support members towards and away from the anterior face of the frame, said slidable connections also orienting the left and right jaw support members so that the posterior ends thereof are always closer than the anterior ends thereof to the anterior face of the frame; and first and second unidirectional clutch means, the first unidirectional clutch means governing the sliding displacement of the left jaw support member towards and away from the anterior face of the frame, the second unidirectional clutch means governing the sliding displacement of the right jaw support member towards or away from the anterior face of the frame, both unidirectional clutch means normally restricting sliding displacement of the left and right jaw support members to a direction away from the anterior face of the frame only, both unidirectional clutch means also providing quick release mechanisms, the quick release mechanisms, when activated, allowing immediate unrestricted sliding displacement of the left and right jaw support members towards the anterior face of the frame;

whereby the anterior face of the frame may be placed under a supine patient's head so that, when the anterior ends of the jaw support members are brought into contact with the angles of the patient's jaw and the patient's jaw is then pushed forward anteriorly, the unidirectional clutch means allow the jaw support members to slidably follow said anterior movement of the jaw and prevent retraction thereof, thereby maintaining or improving the patient's airway in a hands-free environment.

3. The jaw support apparatus of claim 2, further comprising:

first and second stop means, the first stop means defining a predetermined pivotal rest position for the first swinging member with respect to the left extension member as the first swinging member approaches the anterior face of the frame;

the second stop means defining a predetermined pivotal rest position for the second swinging member with respect to the fight extension member as the second swinging member approaches the anterior face of the frame.

4. The jaw support apparatus of claim 2, further comprising first and second elastic means, the first elastic means provided between the first swinging member and the left extension member, the second elastic means provided between the second swinging member and the right extension member, each elastic means operating to encourage the swinging members to approach the anterior face of the frame.

5. The jaw support apparatus of claim 2, further comprising first and second jaw cradles, the first jaw cradle attached to the anterior end of the left jaw support member, the second jaw cradle attached to the anterior end of the right jaw support member, the first and second jaw cradles removable from their respective jaw support members if desired.

6. The jaw support apparatus of claim 5, wherein the first and second jaw cradles each have predetermined three-dimensional profiles, said profiles being sculpted to fit snugly into the angle of a jaw.

7. The jaw support apparatus of claim 5, wherein the first and second jaw cradles each have jaw contact surfaces, the jaw contact surfaces being substantially defined as the area of contact when the jaw cradles are brought into contact with the angles of a jaw, the jaw contact surfaces being made from a first resilient material, whereby comfort is enhanced when the patient's jaw is being supported in the jaw cradles.

8. The jaw support apparatus of claim 7, wherein the first resilient material is rubber.

9. The jaw support apparatus of claim 7, wherein the first resilient material is sponge.

10. The jaw support apparatus of claim 7, wherein the first resilient material is polyurethane.

11. The jaw support apparatus of claim 2, further comprising detachable pillow means, the detachable pillow means removably attached to the anterior face of the frame.

12. The jaw support apparatus of claim 11, wherein the detachable pillow means has a predetermined three-dimensional profile, said profile being sculpted to fit the back of a supine head and neck snugly.

13. The jaw support apparatus of claim 12, wherein the detachable pillow means has a head contact surface, the head contact surface being substantially defined as the area of contact when the detachable pillow means is brought into contact with the back of a supine patient's head and neck, the head contact surface being made from a second resilient material, whereby comfort is enhanced when the patient's head is being supported by the detachable pillow means.

14. The jaw support apparatus of claim 13, wherein the second resilient material is rubber.

15. The jaw support apparatus of claim 13, wherein the second resilient material is sponge.

16. The jaw support apparatus of claim 13, wherein the second resilient material is polyurethane.

17. The jaw support apparatus of claim 2, further comprising means for restraining a head to the anterior face of the frame.

18. The jaw support apparatus of claim 17, wherein the means for restraining a head includes at least one elasticated band.

19. The jaw support apparatus of claim 17, wherein the means for restraining a head includes a plurality of ties.

20. The jaw support apparatus of claim 17, wherein the means for restraining a head includes at least one fastener means.

21. The jaw support apparatus of claim 20, wherein the at least one fastener means includes a buckle.

22. The jaw support apparatus of claim 20, wherein the at least one fastener means includes a contact adhesive.

23. The jaw support apparatus of claim 20, wherein the at least one fastener means includes a contact friction grip.

24. The jaw support apparatus of claim 20, wherein the at least one fastener means includes a hook-and-loop mechanism.

25. The jaw support apparatus of claim 2, wherein the first and second unidirectional clutch means include:

the first and second swinging members each providing an opening therethrough, each opening having an interior surface including a pair of interior facing walls, each opening also having at least one boss located therein, each boss protruding partially into the opening from an interior facing wall;

the left and right jaw support members each having at least one groove, the grooves in the jaw support members and the bosses in the openings provided in matching pairs;

the left and right jaw support members received into the openings in the first and second swinging members respectively, each boss in each opening also simultaneously received slidably into its matching groove so as to permit the jaw support members to slide towards and away from the anterior face of the frame, the bosses as received into their grooves also permitting a predetermined amount of pivotal rotation of the jaw support members about the bosses, said pivotal rotation being permitted between a first travel limit and a second travel limit;

the first and second jaw support members also providing a straight ratchet means, the interior wall of the opening also providing a pawl means, the straight ratchet means and the pawl means being located so as to engage when the jaw support members are rotated about the bosses all the way to the first travel limit, the straight ratchet means and the pawl means being oriented so as to restrict sliding displacement of the jaw support members to a direction away from the anterior face of the frame only, the straight ratchet means and the pawl means also becoming completely disengaged when the jaw support members are rotated about the bosses towards the second travel limit;

whereby the straight ratchet means and the pawl means normally restrict sliding displacement of the jaw support members to a direction away from the anterior face of the frame, but rotation of the jaw support members about the bosses towards the second travel limits will disengage the straight ratchet means and the pawl means, thereby allowing immediate unrestricted sliding displacement of the jaw support members towards the anterior face of the frame.

26. The jaw support assembly of claim 2, wherein the first and second unidirectional clinch means include:

the first swinging member and the second swinging member each further comprising a substantially dihedral front plate and a substantially dihedral back plate fixed rigidly together by spacer means, the front plates and the back plates each having a front side and a back side, the front side of the back plates facing the back side of the front plates, the spacer means providing gaps between the front plates and the back plates, each gap containing first and second bosses, the first boss located on the front side of the back plate and protruding partially into the gap, the second boss located on the back side of the front plate and also protruding partially into the gap, each gap also providing pawl means, the pawl means fixed within the gap and available to be engaged upon from within the gap;

the left and right jaw support members each further providing two grooves, each boss in each gap paired with a groove in a jaw support member, the left and right jaw support members also each further providing straight ratchet means; and the left and right jaw support members received into the gaps in the first and second swinging members respectively, each boss in each gap also simultaneously received slidably into its paired groove so as to permit the jaw support members to slide towards and away from the anterior face of the frame, the left and right jaw support members as received into the gaps also offering their straight ratchet means to the pawl means in each gap, said straight ratchet means and said pawl means oriented so as to restrict the jaw support members to sliding displacement away from the anterior face of the frame only, the bosses as received into their grooves also permitting a predetermined amount of pivotal rotation of the jaw support members about the bosses, said pivotal rotation being permitted between a first travel limit and a second travel limit, the first travel limit being reached when the straight ratchet means and the pawl means fully engage, the second travel means being reached when the straight ratchet means and the pawl means fully disengage;

whereby the straight ratchet means the and pawl means normally restrict sliding displacement of the jaw support members to a direction away from the anterior face of the frame, but rotation of the jaw support members about the bosses towards the second travel limits will disengage the straight ratchet means and the pawl means, thereby allowing immediate unrestricted sliding displacement of the jaw support members towards the anterior face of the frame.

27. A method of maintaining or improving a supine patient's airway in a hands-free environment, comprising the steps of:

placing a frame with frame extensions under the patient's head;

supporting the patient's jaw from the angles with support members attached slidably to the frame extensions, the slidable attachments permitting sliding displacement of the support members towards and away from the frame;

regulating the sliding displacement of the support members with a unidirectional clutch;

orienting the unidirectional clutch so that the support members are restricted to displacement away from the frame until the clutch is released;

thrusting the patient's jaw anteriorly by sliding the support members away from the frame;

holding the anteriorly thrust jaw in place with the unidirectional clutch; and relieving support of the jaw when desired by releasing the unidirectional clutch;

whereby thrusting the jaw anteriorly maintains or improves the patient's airway, while holding the anteriorly thrust jaw in place with the unidirectional clutch frees the hands for other activities.

* * * * *